US005527768A

United States Patent [19]

Sprecker et al.

[11] Patent Number: 5,527,768

[45] Date of Patent: Jun. 18, 1996

[54] USE OF 1-BENZYL CYCLOHEXANOL IN AUGMENTING, ENHANCING OR IMPARTING AROMAS IN OR TO PERFUME COMPOSITIONS, PERFUMED ARTICLES AND COLOGNES AND, OPTIONALLY, SIMULTANEOUSLY REPELLING INSECTS

[75] Inventors: Mark A. Sprecker, Sea Bright; Richard A. Weiss, Pine Brook; Charles E. J. Beck, Summit, all of N.J.

[73] Assignee: International Flavors & Fragrances Inc., New York, N.Y.

[21] Appl. No.: 345,772

[22] Filed: Nov. 22, 1994

[51] Int. Cl.[6] .................... A61K 7/46

[52] U.S. Cl. .................... 512/20; 424/405

[58] Field of Search .................... 512/20; 424/405

[56] References Cited

U.S. PATENT DOCUMENTS 4,306,096 12/1981 Kiwala et al. .................... 568/659
4,604,487 8/1986 Wiegers et al. .................... 568/715

OTHER PUBLICATIONS

Arctander, "Perfume and Flavor Chemicals (Aroma Chemicals)", vol. I, Monograph 1678, Publication date 1969.
Beilstein, E III 6, 526; H 6,584, 1980.
Cook and Hewett, *J. Chem. Soc.*, 1936, pp. 62–69, Title: "The Dehydration of Benzylcyclohexanols".
Brennan, *Chemical Abstracts*, 1947, col. 6662d, (Abstract of *U.S. Public Health Reports*, 62, 1162–5 (1947)).
Linduska, et al, I, *Journal of Economic Entomology*, vol. 39, No. 6, pp. 767–768; Title: "Flea Repellents for Use on Clothing"; col. 2, ctr. of page (1951).
Linduska, et al, II, Journal of Economic Entomology, vol. 40, No. 4, pp. 562–564; Title: "Determining the Repellency of Solid Chemicals to Mosquitoes"; of special interest: p. 564, col. 22, center of column (1960).

*Primary Examiner*—James H. Reamer
*Attorney, Agent, or Firm*—Arthur L. Liberman

[57] ABSTRACT

Described is the use of 1-benzyl cyclohexanol having the structure:

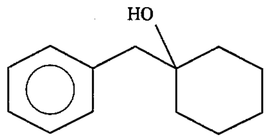

in augmenting or enhancing the aroma of perfume compositions, colognes and perfumed articles such as perfumed polymers and solid or liquid anionic, cationic, nonionic or zwitterionic detergents, fabric softener compositions and fabric softener articles. Also described are processes and compositions for use of the 1-benzyl cyclohexanol of our invention having the structure:

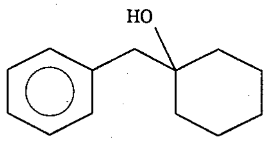

in perfume aroma augmenting, enhancing, modifying and altering compositions and as perfume, cologne and perfumed article aroma imparting compositions. Such compositions may also have imparted thereto as a result of using 1-benzyl cyclohexanol having the structure:

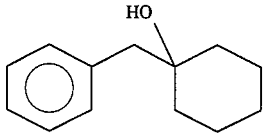

insect repellency.

11 Claims, 3 Drawing Sheets

GLC PROFILE FOR EXAMPLE I

NMR SPECTRUM FOR EXAMPLE I

USE OF 1-BENZYL CYCLOHEXANOL IN AUGMENTING, ENHANCING OR IMPARTING AROMAS IN OR TO PERFUME COMPOSITIONS, PERFUMED ARTICLES AND COLOGNES AND, OPTIONALLY, SIMULTANEOUSLY REPELLING INSECTS

BACKGROUND OF THE INVENTION

The present invention relates to the use in augmenting, enhancing or modifying the aroma of perfume compositions, colognes and perfumed articles of the 1-benzyl cyclohexanol of our invention having the structure:

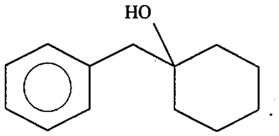

The present invention also relates to perfume compositions, colognes and perfumed articles which also have the property of insect repellency as a result of using 1-benzyl cyclohexanol having the structure:

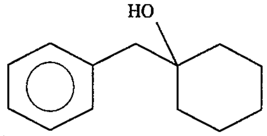

in specified concentration ranges in such compositions.

There has been considerable work performed relating to substances which can be used to impart (or alter, modify or enhance) fragrances to (or in) perfume compositions, colognes or perfumed articles such as solid or liquid anionic, cationic, nonionic or zwitterionic detergents, fabric softener compositions and fabric softener articles as well as perfumed polymers. These substances are used to diminish the use of natural materials some of which may be in short supply and/or to provide more uniform properties to the finished product. There is also a need in creating such perfume compositions, perfumed articles and colognes to enable such compositions of matter to have the property of insect repellency, .particularly against mosquitoes (for example: *Aëdes aegypti* and *Aëdes albopictus*) and against fleas and ticks.

Grapefruit, muguet, blueberry and tea-like aromas with dried fruity topnotes and with grapefruit oil undertones are highly desirable in many types of perfume compositions, perfumed articles and colognes. Phenyl alkanols are well known in the prior art to be useful in perfumery. Thus, for example, the compound having the structure:

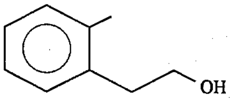

is shown to be so useful in U.S. Pat. No. 4,604,487 issued on Aug. 5, 1986. The compound having the structure:

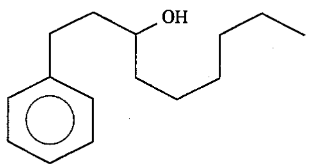

is shown to be so useful by Arctander "Perfume and Flavor Chemicals (Aroma Chemicals)" Volume I 1969 at Monograph No. 1678.

Compounds having a phenyl moiety as well as a cyclohexyl moiety are shown to be useful as fragrance imparting materials and in addition as insect repelling materials. Thus, the compound having the structure:

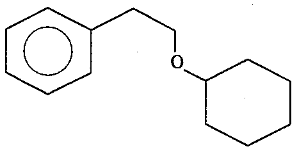

is shown to be so useful in U.S. Pat. No. 4,306,096 issued on Dec. 15, 1981.

Nevertheless, nothing in the prior art explicitly or implicitly discloses the unique utility of the compound having the structure:

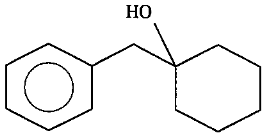

in both augmenting, enhancing or imparting aromas in or to perfume compositions, colognes and perfumed articles as well as in repelling insects such as mosquitoes, ticks and fleas.

However, Linduska and Morton disclose in *Journal of Economic Entomology,* Volume 40, No. 4, pages 562–564, the repellency of 1-benzyl cyclohexanol having the structure:

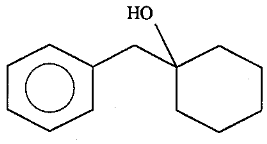

against mosquitoes and Linduska, et al, in the *Journal of Economic Entomology,* Volume 39, No. 6, pages 767–769, disclose the repellency against fleas of the compound having the structure:

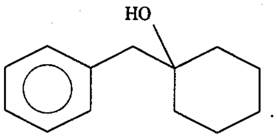

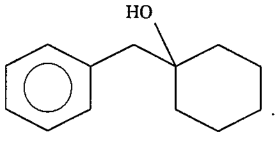

Figure 2:
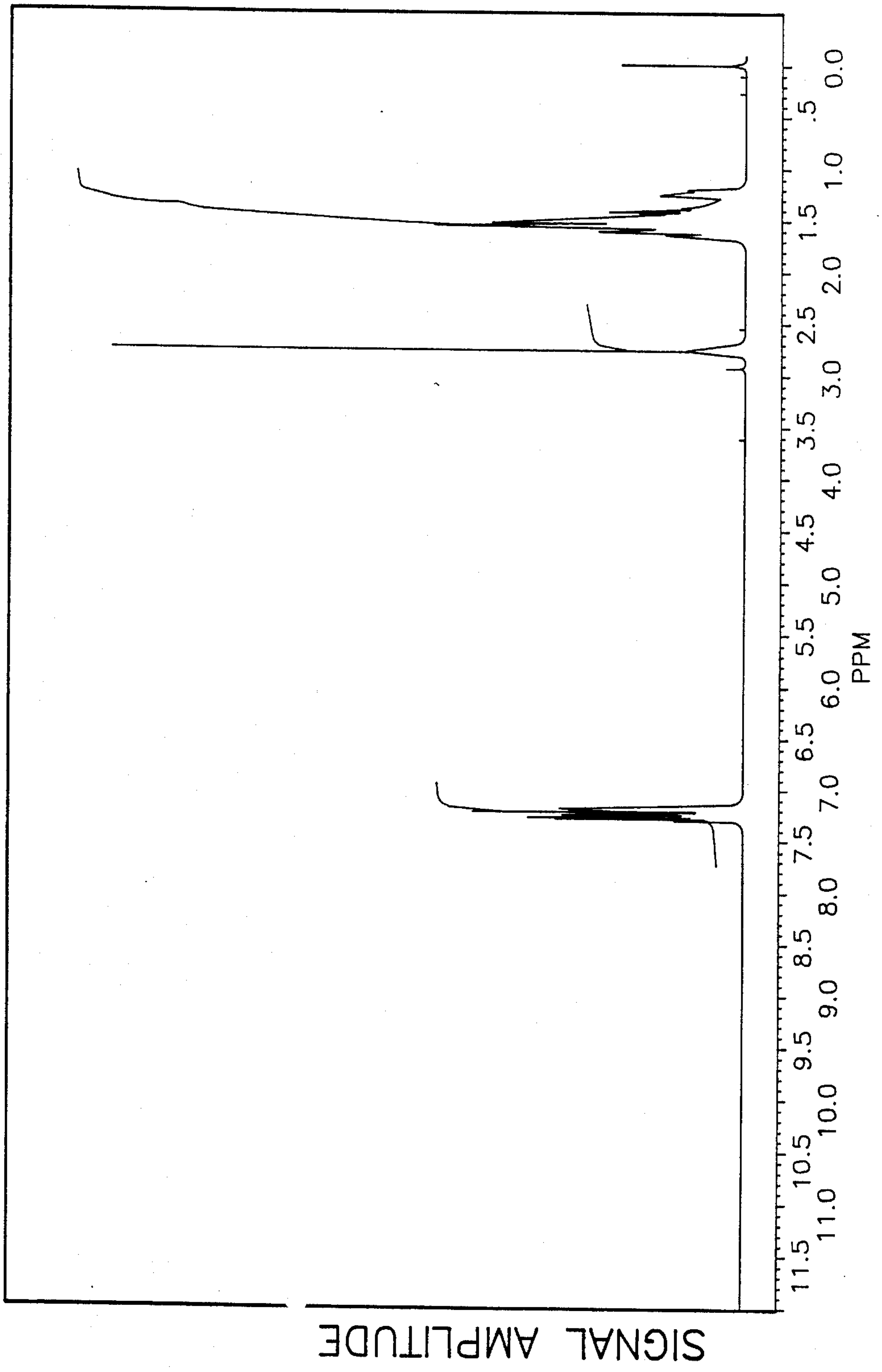

FIG. 2 is the NMR spectrum for the compound having the structure:

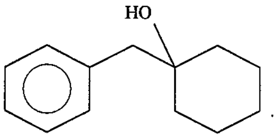

Figure 3:
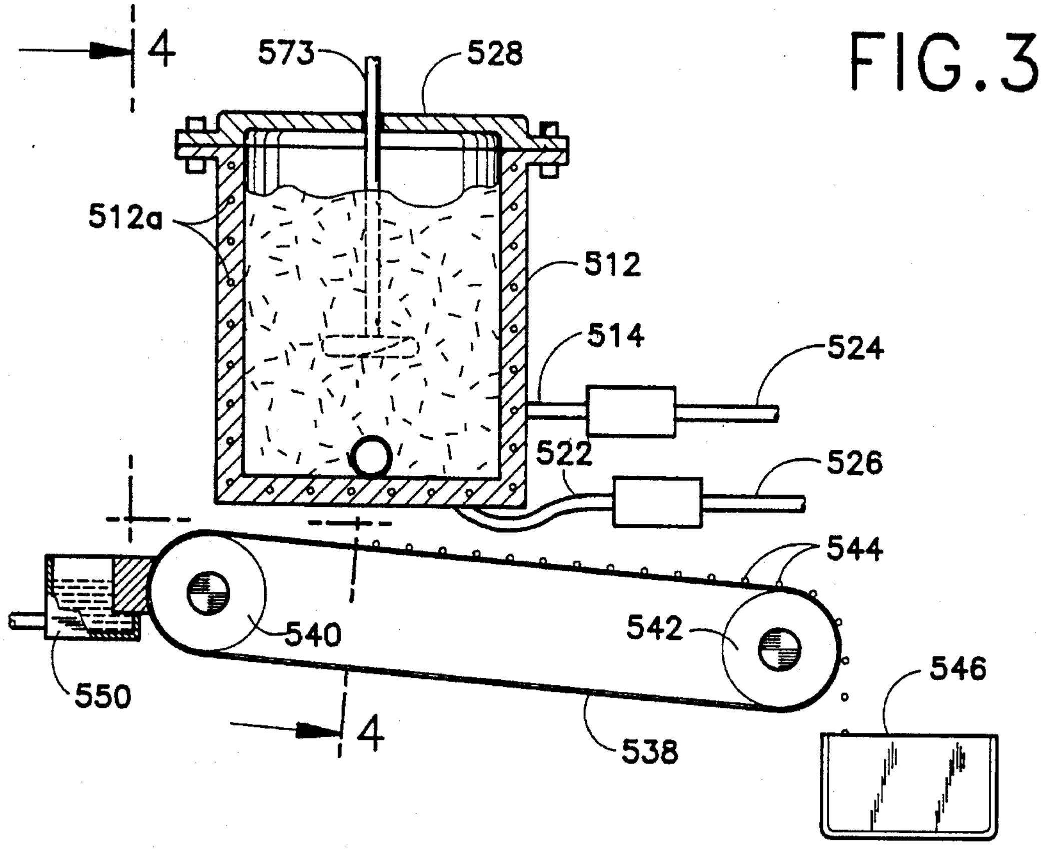

FIG. 3 is a cutaway side elevation view of the apparatus employed for forming a perfumed article of our invention, which perfumed article contains at least the 1-benzyl cyclohexanol of our invention defined according to the structure:

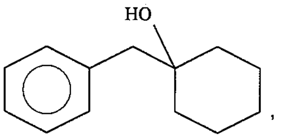

wherein the perfumed article is a microporous polymer containing in the interstices thereof at least the 1-benzyl cyclohexanol of our invention having the structure:

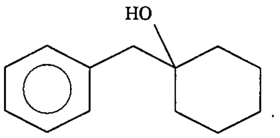

Figure 4:
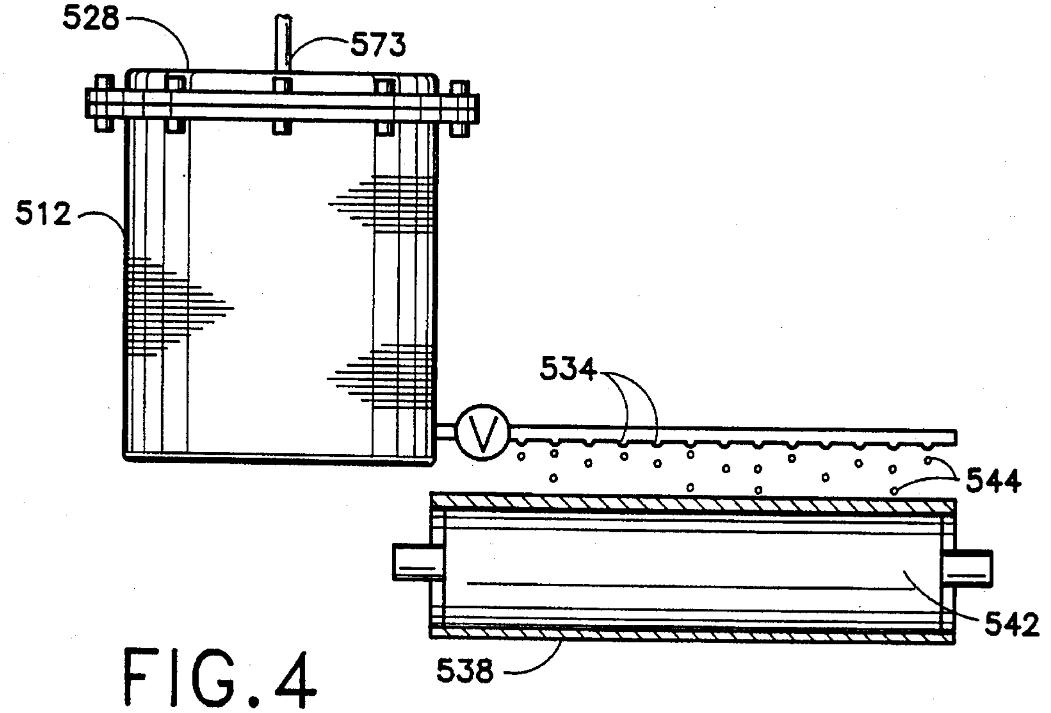

FIG. 4 is a cross-sectional view taken along lines 4—4 of FIG. 3.

DETAILED DESCRIPTION OF THE DRAWINGS

Figure 1:
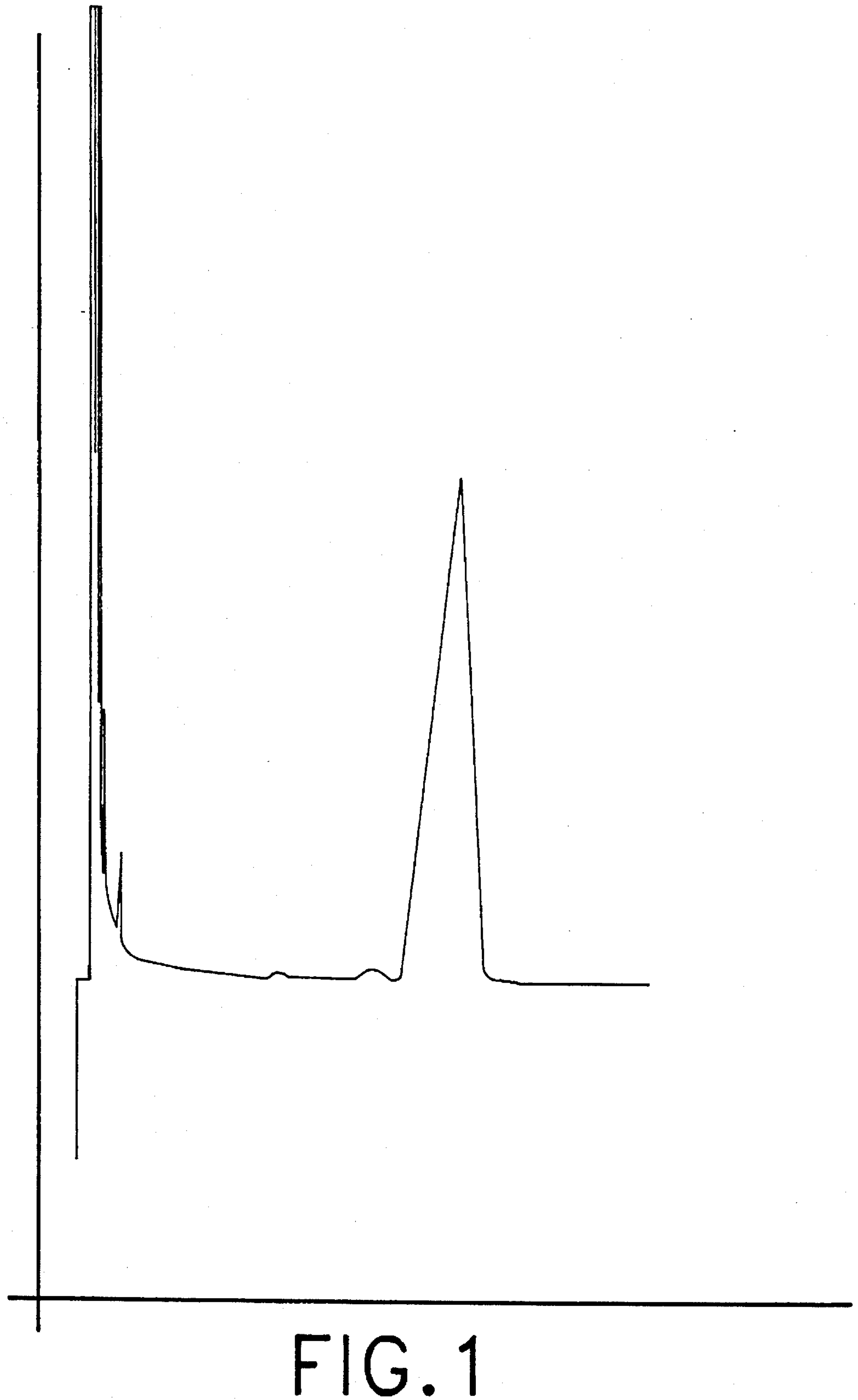
FIG. 1 is the GLC profile for the reaction product of Example I for the preparation of the compound having the structure.

FIG. 1 is the GLC profile for the reaction product of Example I containing the compound having the structure:

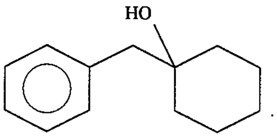

The peak indicated by reference numeral 10 is the peak for the compound having the structure:

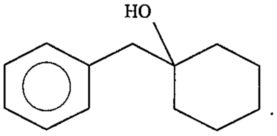

The peak indicated by reference numeral 12 is the peak for the solvent used in the reaction for preparing the compound having the structure:

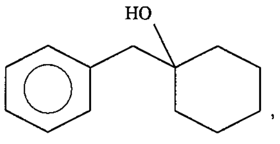

acetic acid in admixture with cyclohexanone.

Referring to FIGS. 3 and 4 which show the apparatus for preparing scented polymers such as polyethylene, a quantity of thermoplastic polymer having a melting point of 220°–250° F. is placed in a container 512 as illustrated in FIGS. 3 and 4. 25 Pounds of a perfume formulation containing the 1-benzyl cyclohexanol of our invention is then quickly added to the liquified molten polymer in container 512, the lid 528 is put in place and the agitating means 573 are actuated. The temperature is maintained at about 225° F. and the mixing is continued for about 5–15 minutes. The valve "V" is then opened to allow flow of the molten thermoplastic polymer (e.g., polyethylene), enriched with a scent-imparting substance containing the 1-benzyl cyclohexanol of our invention, to exit through orifices 534. The liquid falling through orifices 534 solidifies almost instantaneously upon impact of the moving cooled conveyor 538. Thermoplastic polymer (e.g., polyethylene) beads or pellets 544 having a pronounced scent as described in the examples, infra, resulting from the composition containing the 1-benzyl cyclohexanol of our invention are thus formed. Analysis demonstrates that the pellets contain about 25% of a scent-imparting material and an insect-repelling material (repelling *Aëdes aegypti* and repelling ticks and fleas) containing the 1-benzyl cyclohexanol of our invention so that almost no loss in the scenting and insect repelling substance occurs. The pellets are used as set forth, infra. the conveyor belt 538 is driven by rollers 540 and 542 with cooling apparatus 550 next to roller 540. The tank 512 is heated with heating elements 512A which are energized using an electric energy source evolved via wires 524/514 and 526/522. The solidified pellets are collected in container 546 for a subsequent utilization as set forth in the examples, infra.

THE INVENTION

This invention relates to the 1-benzyl cyclohexanol of our invention having the structure:

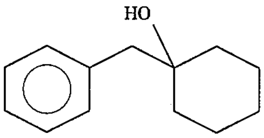

and uses thereof in augmenting or enhancing a variety of fragrances of various consumable materials. The 1-benzyl cyclohexanol of our invention when used in polymers at levels of between 5 and 45% by weight (for example polyethylene) acts as both an insect repellent and an agent which augments or enhances or imparts aroma in or to perfume compositions, perfumed articles and colognes wherein the perfumed articles may be solid or liquid anionic, cationic, nonionic or zwitterionic detergents, fabric softeners, dryer-added fabric softener articles, hair conditioners, deodorants and cosmetic powders.

The 1-benzyl cyclohexanol of our invention having the structure:

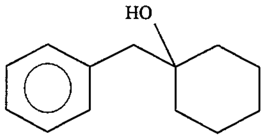

has a grapefruit, muguet, blueberry, tea-like aroma with dried fruity topnotes and grapefruit oil undertones.

The 1-benzyl cyclohexanol of our invention when used in candles, polymers and insect repellent soaps at levels of:

(i) from about 0.05 up to about 5% by weight in soaps;

(ii) from about 5 up to about 45% by weight in microporous polymers; and (iii) from about 1 up to about 30% by weight in candles fragrances the environment surrounding the soaps, candles and polymers by causing the environment to have a grapefruit, muguet, blueberry, tea-like aroma with dried fruity topnotes and grapefruit oil undertones and, in addition, repels mosquitoes, ticks and fleas from the environment surrounding said articles when that environment is inhabited by such mosquitoes, ticks and fleas. The species of mosquitoes repelled are *Aëdes aegypti* and *Aëdes albopictus* as well as *Anopheles quadrimaculatus* and the species of fleas are *Ctenocephalides canis* (Curt.) and *C. felis.*

The species of ticks repelled are *Amblyomma americanum.*

The 1-benzyl cyclohexanol of our invention is disclosed to repel such ticks in *Chem. Abstracts* 1948, 3897h, abstract of *U.S. Pub. Health Rpts.* 63, 339–46 (1948).

Thus, our invention is directed to fragrance compositions, cologne compositions and perfumed article compositions which are intended to impart, augment or enhance fragrances as well such compositions intended not only to impart, augment or enhance fragrances but also to repel insects.

The 1-benzyl cyclohexanol of our invention having the structure:

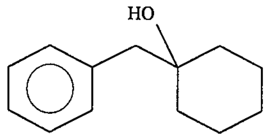

may be prepared by reacting cyclohexanone with benzyl magnesium halide such as benzyl magnesium chloride according to the reaction:

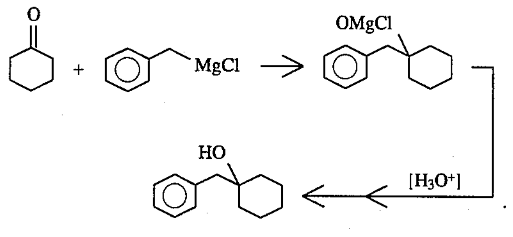

This reaction is well known in the prior art as disclosed by Newkome, et al, "The preparation and dehydration of 1-benzyl cycloalkanols" *Journal of Chemical Education,* Volume 15, No. 5, May 1973, pages 372 and 273 (the content of which is incorporated herein by reference).

The 1-benzyl cyclohexanol of our invention having the structure:

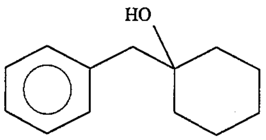

can be used to contribute grapefruit, muguet, blueberry, tea-like aromas with dried fruity topnotes and grapefruit oil undertones to perfume compositions, perfumed articles and colognes. As an olfactory agent, the 1-benzyl cyclohexanol of our invention can be formulated into or used as components of a "perfume composition" or can be used as components of a "perfumed article" or the perfume composition may be added to perfumed articles. When added at levels of between 0.05% up to 45% by weight of the perfumed article or the perfume composition, the 1-benzyl cyclohexanol of our invention also acts to reduce attractancy and increase repellency against mosquitoes, ticks and fleas including the following species:

(i) mosquitoes:
*Aëdes aegypti;*
Anopheles quadrimaculatus;

(ii) fleas:
*Ctenocephalides canis* (Curt.);
*C. felis* (Bouché);

(iii) ticks:
*Amblyomma americanum.*

The term "perfume composition" is used herein to mean a mixture of organic compounds including, for example, alcohols (other than the 1-benzyl cyclohexanol of our invention), aldehydes, ketones, nitriles, ethers, lactones, natural essential oils, synthetic essential oils and frequently hydrocarbons which are admixed so that the combined odors of the individual components produce a pleasant or desired fragrance. Such perfume compositions usually contain: (a) the main note or the "bouquet" or foundation-stone of the composition; (b) modifiers which round off and accompany the main note; (c) fixatives which include odorous substances which lend a particular note to the perfume throughout all stages of evaporation, and substances which retard evaporation; and (d) topnotes which are usually low-boiling, fresh-smelling materials.

In perfume compositions, the individual component will contribute its particular olfactory characteristics, but the overall effect of the perfume composition will be the sum of the effects of each of the ingredients. Thus, the 1-benzyl cyclohexanol of our invention or mixtures thereof with other perfumery materials can be used to alter the aroma characteristics of a perfume composition, for example, by highlighting or moderating the olfactory reaction contributed by another ingredient in the composition.

The amount of the 1-benzyl cyclohexanol of our invention which will be effective in perfume compositions depends on many factors, including the other ingredients, their amounts and the effects which are desired (including insect repellency or diminution of insect attractancy). It has been found that perfume compositions containing as little as 0.05% of the 1-benzyl cyclohexanol of our invention, or even less, can be used to impart interesting grapefruit, muguet, blueberry, and tea-like aromas with dried fruity topnotes and grapefruit oil undertones to soaps, liquid and solid cationic, anionic, nonionic or zwitterionic detergents, cosmetics, powders, liquid and solid fabric softeners, perfumed polymers per se such as polyethylene and polypropylene, optical brightener compositions and other products. The amount employed can range up to 50% or higher and will depend on considerations of cost, nature of the end product, and the effect desired on the finished product and particular fragrance sought; as well as the degree of insect repellency or degree of diminution of insect attractancy desired.

The 1-benzyl cyclohexanol of our invention having the structure:

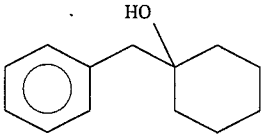

can be used alone or in a perfume composition as an olfactory component in detergents and soaps, space odorants and deodorants; perfumes; colognes, toilet waters; bath salts; hair preparations such as lacquers, brilliantines, pomades and shampoos; cosmetic preparations such as creams, deodorants, hand lotions and sun screens; powders such as talcs, dusting powders, face powders and the like. When used as an olfactory component of a perfumed article, as little as 0.05% of the 1-benzyl cyclohexanol of our invention will suffice to impart an interesting, substantive, long-lasting grapefruit, muguet, blueberry and tea-like aroma with dried fruity topnotes and grapefruit oil undertones. Generally, no more than 0.5% is required in the perfumed article, but this amount is not limiting and the amount can be much greater. Accordingly, the perfumed articles of our invention preferably contain from about 0.05% up to about 0.5% by weight of the perfumed article of the 1-benzyl cyclohexanol of our invention; with the exception of perfumed polymers wherein the amount can go as high as 45% as stated, supra.

In addition, the perfume composition of our invention can contain a vehicle or carrier for the 1-benzyl cyclohexanol of our invention alone or with other ingredients. The vehicle can be a liquid such as an alcohol such as ethanol, a glycol such as propylene glycol or 1,6 hexylene glycol, or the like. The carrier can be an absorbent solid such as a gum (e.g., guar gum or xanthan gum or gum arabic) or components for encapsulating the composition such as gelatin (as by coacervation) or a urea formaldehyde prepolymer (to form a urea formaldehyde polymer wall around a liquid perfume center) which can be used to form a capsule wall surrounding the perfume oil.

It will thus be apparent that the 1-benzyl cyclohexanol of our invention can be utilized to alter, modify, augment or enhance sensory properties particularly organoleptic properties such as fragrances in a wide variety of consumable materials.

The following Example I serves to illustrate a process for preparing the 1-benzyl cyclohexanol of our invention. The examples following Example I serve to illustrate our invention and this invention is to be considered restricted thereto only as indicated in the appended claims.

All parts and percentages given herein are by weight unless specified.

EXAMPLE I

PREPARATION OF 1-BENZYL CYCLOHEXANOL

Reaction

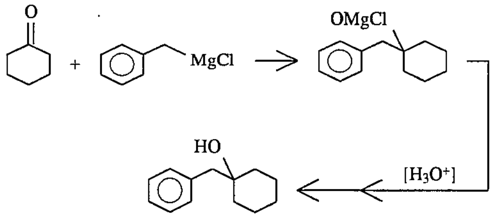

Into a 2 liter reaction vessel equipped with stirrer, thermometer, heating mantle and reflux condenser is placed 800 ml of 2 molar benzyl magnesium chloride (1.6 moles) in diethyl ether. The benzyl magnesium chloride solution is cooled to 10°–15° C.

Over a period of one hour, 147 grams of cyclohexanone (1.5 moles) is added to the reaction mass while maintaining the reaction mass at 15°–20° C.

The reaction mass is stirred for a period of one hour at 15°–200° C.

The reaction mass is then quenched with 120 ml of acetic acid and poured onto 600 grams of ice.

The organic phase is separated from the aqueous phase and the organic phase is washed with 400 ml of 10% sodium bicarbonate (pH=8).

The reaction mass is then fractionally distilled yielding the following fractions:

| Fraction Number | Vapor Temperature (°C.) | Liquid Temperature (°C.) | Vacuum mm/Hg. Pressure |
|---|---|---|---|
| 1 | 23/27 | 23/100 | 100/150 |
| 2 | 86 | 135 | 1 |
| 3 | 132 | 138 | 1.5 |
| 4 | 126 | 185 | 2 |

Fractions 2 and 3 are bulked. Bulked distillation Fractions 2 and 3 are confirmed to be the compound having the structure:

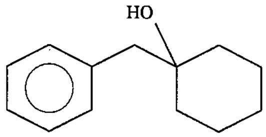

by NMR, IR and mass spectral analysis.

FIG. 1 is the GLC profile for the reaction product containing the compound having the structure:

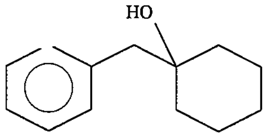

(conditions: SE-30 column programmed at 180° C. isothermal). The peak indicated by reference numeral 10 is the peak for the compound having the structure:

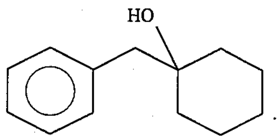

The peak indicated by reference numeral 12 is the peak for the solvent of the reaction which is a mixture of diethyl ether, and acetic acid.

FIG. 2 is the NMR spectrum for the compound having the structure:

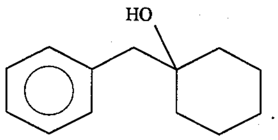

The compound having the structure:

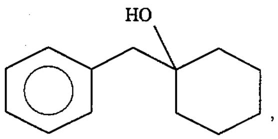

bulked distillation Fractions 2 and 3 have a grapefruit, muguet, blueberry, tea-like aroma with dried fruity topnotes and grapefruit oil undertones.

EXAMPLE II

A GREEN FLORAL FRAGRANCE

The following mixture is prepared:

| Ingredients | Parts by Weight |
|---|---|
| 3-Phenyl-4-pentenal ethylene acetal | 3.0 |
| 3-Phenyl-4-pentenal diisobutyl acetal | 4.0 |
| 2-oxa-1,1,3,3-tetramethyl-2,3,5,6,7,8-hexahydro-1H-benz(f)-indane | 3.0 |
| Ylang extra | 5.0 |
| Geraniol coeur | 100.0 |
| Citronellol coeur | 70.0 |
| Dimethyl benzyl carbinol | 20.0 |
| Phenyl ethyl alcohol coeur | 30.0 |
| Hexyl cinnamic aldehyde | 30.0 |
| 2-n-heptyl-cyclopentanone | 2.0 |
| Linalyl acetate | 30.0 |
| n-Decanal | 2.0 |
| Geranonitrile | 30.0 |
| Orange terpenless | 10.0 |
| Geranyl acetate | 10.0 |
| Nerol | 20.0 |
| 1-Benzyl cyclohexanol having the structure: 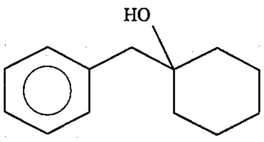 prepared according to Example I, supra, bulked distillation Fractions 2 and 3 | 120.0 |

The compound having the structure:

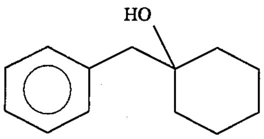

prepared according to Example I, supra, imparts to this green floral fragrance a substantive, long lasting grapefruit, muguet, blueberry, tea-like, grapefruit oil undertone profile and dried fruity topnotes. Accordingly, the fragrance of Example II can be described as:

"a green floral aroma with grapefruit, grapefruit oil, muguet, blueberry, and tea-like undertones and dried fruity topnotes".

EXAMPLE III

PREPARATION OF A COSMETIC POWDER COMPOSITION

A cosmetic powder is prepared by mixing in a ball mill 100 grams of talcum powder with 0.25 grms of the perfume substance set forth in Table I below. The resulting cosmetic powders have excellent aroma profiles as indicated in Table I below.

TABLE I

| Perfume Substance | Aroma Profile Imparted |
|---|---|
| Compound having the structure: 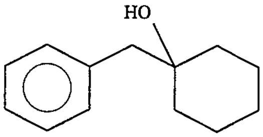 prepared according to Example I bulked distillation Fractions 2 and 3. | A grapefruit, muguet, blueberry, tea-like aroma with dried fruity topnotes and grapefruit undertones. |
| Perfume composition of Example II. | A green floral aroma with grapefruit, grapefruit oil, muguet, blueberry, and tea-like undertones and dried fruity topnotes. |

EXAMPLE IV

PREPARATION OF SOAP COMPOSITION

100 Grams of soap chips are mixed with 1 gram of each of the perfume materials of Table I of Example III until a substantially homogeneous composition is obtained. The resulting mixture is melted and maintained at 10 atmospheres pressure at a temperature of 180° C. for a period of 4 hours. At the end of the 4-hour period, the resulting homogeneous mixture is cooled. The perfumed soap composition manifests an excellent aroma character as set forth in Table I of Example III.

EXAMPLE V

PREPARATION OF A DETERGENT COMPOSITION

A granular detergent composition is prepared according to Example 9 of Canadian Patent No. 1,004,566 (the disclosure of which incorporated by reference herein) containing the following ingredients:

| Ingredients | Parts by Weight |
|---|---|
| Anhydrous sodium carbonate | 30.0 |
| Hydrated sodium silicate (81.5% solids, $SiO_2$:$Na_2O$ ratio 2.1:1 by weight) | 20.0 |
| Coconut alcohol condensed with 6 molar proportions of ethylene oxide | 10.0 |
| Sodium citrate dihydrate | 10.0 |
| Sodium dichlorocyanurate dihydrate | 3.8 |
| Polyethylene glycol (available under the trademark Carbowax 4000, M.W. 3000–3700) | 2.0 |
| Dimethyl silicone | 0.8 |
| Anhydrous sodium sulfate | 15.5 |
| Perfume substance as set forth in Table I of Example III | 5.9 |

The resulting detergent compositions have excellent aromas as set forth in Table I of Example III.

EXAMPLE VI

PREPARATION OF A DETERGENT COMPOSITION

A detergent is prepared from the following ingredients according to Example I of Canadian Patent No. 1,007,948 (the disclosure of which is incorporated herein by reference):

| Ingredients | Parts by Weight |
|---|---|
| Neodol 45-11 (a $C_{14}$–$C_{15}$ alcohol ethoxylated with 11 moles of ethylene oxide) | 12.0 |
| Sodium carbonate | 55.0 |
| Sodium citrate | 20.0 |
| Sodium sulfate, water brighteners | q.s. |

This detergent is a phosphate-free detergent. A total of 100 grams of this detergent is admixed individually with 0.15 grams of each of the perfumery substances of Table I of Example III, supra. Each of the detergents has excellent aromas as set forth in Table I of Example III.

EXAMPLE VII

PERFUMED LIQUID DETERGENT

Concentrated liquid detergents with aroma nuances as set forth in Table I of Example III containing a 0.10%, 0.15% and 0.20% of each of the perfumery substances of Table I of Example III are prepared. They are prepared by adding and homogeneously admixing the appropriate quantity of each of the perfumery substances of Table I of Example III in the liquid detergent. The detergents all possess excellent aromas as Set forth in Table I of Example III.

EXAMPLE VIII

COLOGNE AND HANDKERCHIEF PERFUMES

The perfume substances of Table I of Example III are each incorporated separately into colognes at concentrations of 1.5%, 2.0%, 2.5%, 3.0%, 4.0% and 5.0% in 70%, 75%, 80%, 85% and 90% aqueous ethanol solutions; and into handkerchief perfumes at concentrations of 15%, 20%, 30%, and 40% (in 80%, 85%, 90% and 95% aqueous ethanol solutions) Distinct and definitive strong fragrances are imparted to the colognes and to the handkerchief perfumes at the levels indicated according to the aroma profiles as set forth in Table I of Example III.

EXAMPLE IX

Utilizing the procedure of Example I of column 15 of U.S. Pat. No. 3,632,396, a nonwoven cloth substrate useful as a dryer-added fabric-softening article of manufacture is prepared wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):
   57 percent C2--22 HAPS;
   22 percent isopropyl alcohol;
   20 percent antistatic agent;
   1 percent of the 1-benzyl cyclohexanol of our invention as set forth in Table I of Example III and giving rise to the aroma nuances as set forth in said Table I of Example III.

Fabric-softening compositions prepared as set forth above having the above aroma characteristics essentially consist of a substrate having a weight of about 3 grams per 100 square inches, a substrate and an outer coating of about 1.4 grams per 100 square inches of substrate, thereby providing a total aromatized substrate and outer coating weight ratio of about 1:1 by weight of the substrate. The aromas as set forth in Table I of Example III, supra, above are imparted in a pleasant manner to the head space in the dryer on operation thereof using the said dryer-added fabric-softening nonwoven fabric.

EXAMPLE X

Scented polyethylene pellets having a pronounced aroma as set forth in Table I of Example III, supra, are prepared as follows:

75 Pounds of polyethylene having a melting point of about 220° F. is heated to about 230° F. in a container of the kind illustrated in FIGS. 3 and 4. 25 Pounds of one of the perfume compositions of Table I of Example III is then quickly added to the liquified polyethylene, the lid 528 is put in place and the agitating means 573 are actuated. The temperature is maintained at about 225° F. and the mixing is continued for about 5–15 minutes. The valve "V" is then opened to allow flow of the molten polyethylene enriched with the perfume substance (one of the materials of Table I of Example III) to exit through the orifices 534. The liquid falling through the orifices 534 solidifies almost instantaneously upon impact with the moving cooled conveyor 538. Polyethylene beads or pellets 544 having pronounced aromas as set forth in Table I of Example III are thus formed. Analysis demonstrates that the pellets contain about 25% of the perfume substance of Table I of Example III so that almost no losses in the scenting substance did occur. These pellets may be called "master pellets".

50 Pounds of the scent containing "master pellets" are than added to 1,000 pounds of unscented polyethylene powder and the mass is heated to the liquid state. The liquid is molded into thin sheets of films. The thin sheets of films have pronounced aromas as set forth in Table I of Example III. The sheets of films are cut into strips ¼ inches in width×3 inches in length and placed into apparatus used for air fresheners. On operation of said apparatus as a room freshener, after 4 minutes, the room has an aesthetically pleasing aroma as set forth in Table I of Example III.

EXAMPLE XI

100 Pounds of polypropylene are heated to about 300° F. 30 Pounds of one of the essences as described in Table I of Example III, supra, are added to the liquified polypropylene. The procedure is carried out in the apparatus shown in FIGS. 3 and 4. After mixing for about 8 minutes, the valve "V" is opened to allow the exit of the polypropylene scented material whereby solid pellets having pronounced aromas as set forth in Table I of Example III are formed on the conveyor. The pellets thus obtained are then admixed with about twenty times their weight of unscented polypropylene and the mixture is heated and molded into "spaghetti" tows. The spaghetti tows are cut into small cylinders approximately 0.1 inch in length×0.02 inch in diameter. The cylinders have a strong and pleasant perfumed smell and scents as set forth in Table I of Example III.

The cylinders are used in apparatus for air freshening and on operation of said apparatus, the environment surrounding the air freshener has a pleasant and faint aroma as set forth in Table I of Example III.

What is claimed is:

1. A process for augmenting or enhancing the aroma of a consumable material comprising the step of adding to said consumable material an aroma imparting, augmenting or enhancing quantity or concentration of 1-benzyl cyclohexanol defined according to the structure:

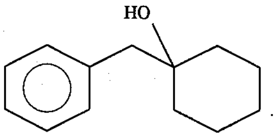

2. The process of claim 1 wherein the consumable material is a perfume composition.

3. The process of claim 1 wherein the consumable material is a perfumed article.

4. The process of claim 1 wherein the consumable material is a cologne.

5. The process of claim 1 wherein the consumable material is a microporous polymer and the compound having the structure:

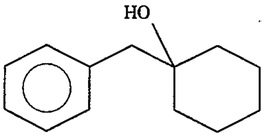

is contained in the interstices of said microporous polymer.

6. A consumable material selected from the group consisting of perfume compositions, colognes and perfumed articles consisting of a perfume base, a cologne base or a perfumed article base and intimately admixed therewith an aroma imparting, augmenting or enhancing quantity of the 1-benzyl cyclohexanol having the structure:

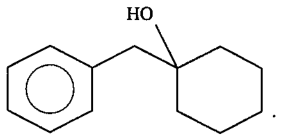

7. The consumable material of claim 6 which is a perfume composition.

8. The consumable material of claim 6 which is a cologne.

9. The consumable material of claim 6 which is a perfumed article.

10. The consumable material of claim 6 which is a microporous polymer and contained in the interstices thereof 1-benzyl cyclohexanol having the structure:

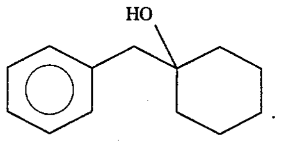

11. A process for imparting an aroma to a volume inhabited by an insect species selected from the group consisting of:

*Aëdes aegypti;*

Anopheles quadrimaculatus;

Ctenocephalides canis (Curt.);

*C. felis* (Bouché); and

*Amblyomma americanum;* and simultaneously repelling said insect species from said volume comprising the step of introducing into said volume 1-benzyl cyclohexanol having the structure:

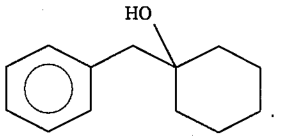

* * * * *